United States Patent [19]

White, V et al.

[11] 4,281,246

[45] Jul. 28, 1981

[54] CONTINUOUS-FLOW SOLUTION CONCENTRATOR AND LIQUID CHROMATOGRAPH/MASS SPECTROMETER INTERFACE AND METHODS FOR USING BOTH

[75] Inventors: Edward White, V; Harry S. Hertz; Richard G. Christensen, all of Gaithersburg, Md.

[73] Assignee: The United States of America as represented by the Administrator of the United States Environmental Protection Agency, Washington, D.C.

[21] Appl. No.: 84,273

[22] Filed: Oct. 12, 1979

[51] Int. Cl.³ .................. B01D 59/44; B01D 1/22
[52] U.S. Cl. .................... 250/282; 250/289; 73/61.1 C; 159/13 R; 159/49
[58] Field of Search .............. 250/281, 282, 288, 289; 73/61.1 C; 159/13 R, 13 B, 49

[56] References Cited

U.S. PATENT DOCUMENTS

| | | |
|---|---|---|
| 2,601,097 | 6/1952 | Crawford .................. 250/288 |
| 3,080,746 | 3/1963 | Nerheim ................... 73/61.1 C |
| 3,896,661 | 7/1975 | Parkhurst et al. . |
| 3,929,004 | 12/1975 | Gunew et al. . |
| 3,997,298 | 12/1976 | McLafferty et al. . |
| 4,055,987 | 11/1977 | McFadden . |
| 4,112,297 | 9/1978 | Miyagi et al. . |

Primary Examiner—Bruce C. Anderson

[57] ABSTRACT

An interface between a liquid chromatograph and a mass spectrometer is provided for conducting a liquid stream from the chromatograph to the spectrometer. The stream passes from the chromatograph continuously along a tapered concentrator wire toward the narrow end of the wire. The stream is heated in order to evaporate solvent therefrom and to increase the concentration of the solute therein. When the stream reaches the narrow end of the wire, the vacuum created by the mass spectrometer draws the stream through an elongated capillary tube which has a pointed carrier wire positioned therein. A gap is provided in the tube where the tube and the carrier wire intersect the concentrator wire. The capillary tube is either formed with a reduced diameter at one end adjacent the spectrometer or the carrier wire has a ball of solder at that end in order to partially restrict the flow through the tube. The carrier wire is longitudinally moveable within the tube in order to control the flow of material into the spectrometer. Other uses for the tapered and heated wires are contemplated for removing solvent from a liquid stream in order to diminish the stream's flow rate or to increase the concentration of the solute of such a stream. Methods for conducting liquid from a liquid chromatograph to a mass spectrometer and for removing solvent from a liquid stream are also disclosed.

35 Claims, 4 Drawing Figures

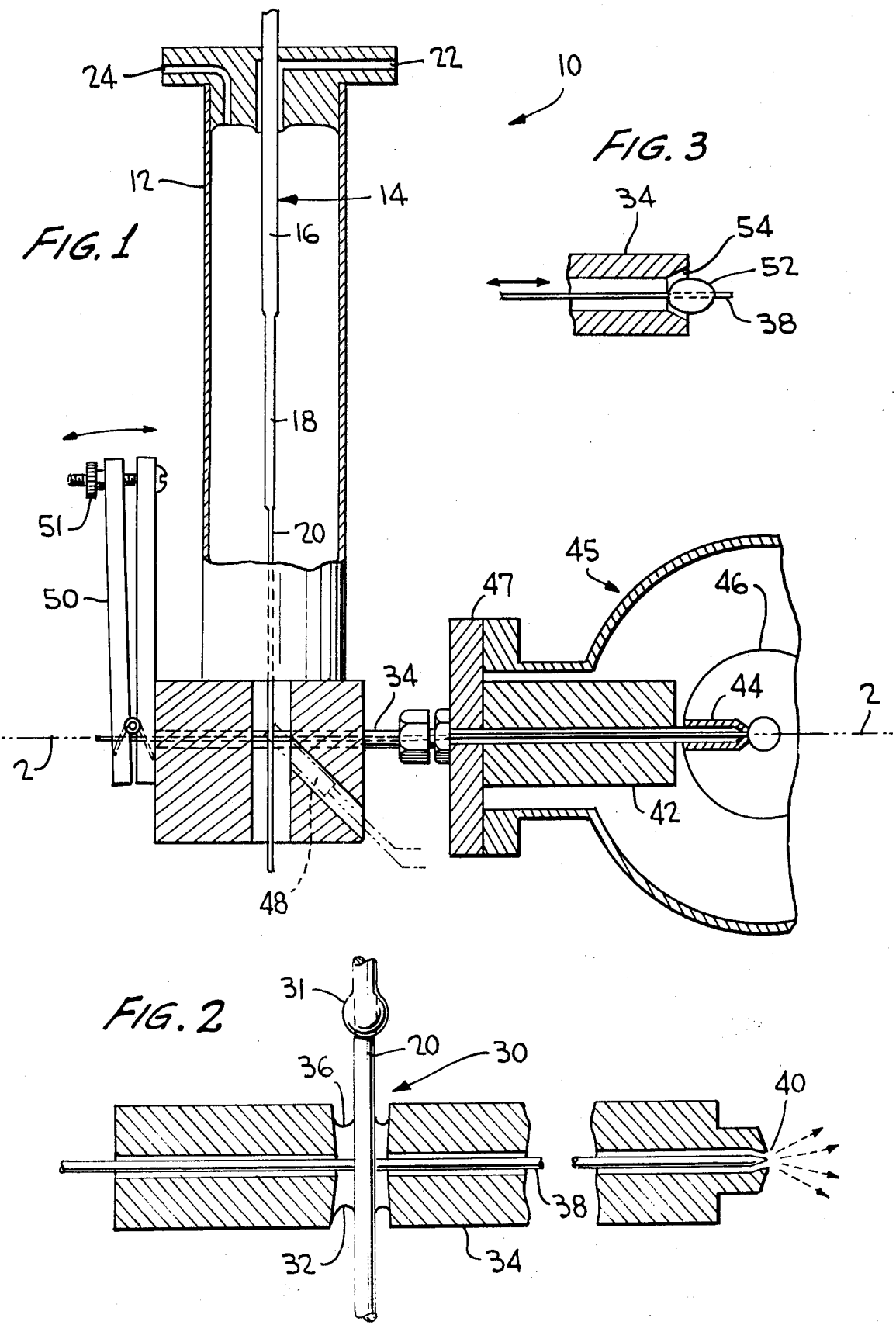

CONTINUOUS-FLOW SOLUTION CONCENTRATOR AND LIQUID CHROMATOGRAPH/MASS SPECTROMETER INTERFACE AND METHODS FOR USING BOTH

BACKGROUND OF THE INVENTION

1. FIELD OF THE INVENTION

The present invention relates generally to an interface between a liquid chromatograph and a mass spectrometer and more particularly to an interface for conducting the liquid effluent from the chromatograph to the spectrometer. Apparatus for continuously concentrating the effluent is also provided.

2. DESCRIPTION OF THE PRIOR ART

Several attempts have been made to provide an interface between a liquid chromatograph and a mass spectrometer. Additionally, attempts have been made to concentrate a liquid stream by evaporating the solvent from the stream.

McFadden, U.S. Pat. No. 4,055,987, discloses a liquid chromatograph/mass spectrometer interface for permitting the introduction of a solution from the chromatograph to the spectrometer. A metallic ribbon in the form of a loop is moveable and is utilized to deliver the liquid stream to the spectrometer, and a heat source is provided for heating the stream in order to achieve preliminary evaporation.

McLafferty et al., U.S. Pat. No. 3,997,298, discloses an apparatus and method for continuously introducing an eluted effluent from a liquid chromatograph into the ionization chamber of a mass spectrometer. The apparatus includes a restricted capillary tube for introduction of the mixture into the chamber and is designed to slow the entrance of solution into the spectrometer to a small percentage of the normal flow rate of the effluent.

Miyagi et al., U.S. Pat. No. 4,112,297, discloses a liquid chromatograph/mass spectrometer interface for introducing a nebulized effluent sample to the ion source of a mass spectrometer. The interface includes an evaporator having a heater for evaporating only the solvent in the nebulized effluent from the chromatograph.

Other prior art interfaces are disclosed for transporting a liquid stream from the chromatograph by means of a pretreated conveyor belt as well as by vaporizing the solvent by heating, vacuum, and/or an inert gas flow. Such teachings can be found in German Pat. Nos. 2,654,057 and 2,811,300.

Other devices broadly disclose the use of heating for evaporating a solvent. Parkhurst, U.S. Pat. No. 3,896,661, discloses a method and apparatus for coupling a thin-layer chromatography system with a mass spectrometer. The analytes in the chromatograph are sublimed by heat into a spectrometer ion source.

Gunew et al., U.S. Pat. No. 3,929,004, discloses a device for conveying a liquid stream used in conjunction with an analysis of the material suspended within the stream. The stream is retained by a wire mesh conveyor and is heated in order to volatilize the liquid and leave a residue on the conveyor, which residue is then transported into a gas chromatography mass flow detector.

SUMMARY OF THE INVENTION

Accordingly, it is a general object of the present invention to provide a new and improved interface between a liquid chromatograph and a mass spectrometer.

Another object of the present invention is to provide a new and improved structure for removing solvent from a liquid stream in order to increase the concentration of a solute while the liquid stream is continuously flowing about a concentrator wire.

A further object of the present invention is to provide a new and improved structure which can be used when it is desired to diminish the flow rate of a liquid stream or to increase the concentration of a solute in a liquid stream. Yet another object of the present invention is to provide a new and improved interface between the liquid chromatograph and a mass spectrometer which will control the rate of flow of chromatograph effluent into the ion source of the spectrometer.

Upon further study of the specification and claims, further objects and advantages of this invention will become apparent to those skilled in the art.

Briefly, the above and other objects of the present invention are attained in one aspect thereof by providing an interface between a liquid chromatograph and a mass spectrometer for introducing a liquid stream from the chromatograph into the spectrometer. The interface includes a tapered wire which decreases from a first end having a relatively wide diameter to a second end having a relatively narrow diameter so that the wire continuously carries the stream towards the narrow end. Means for heating the stream are provided in order to convert part of the stream into vapor. Additionally, means for then drawing the stream from adjacent the second end and for conducting the stream into the mass spectrometer are also provided.

BRIEF DESCRIPTION OF THE DRAWINGS

The above and other objects, features and advantages of the present invention will be more fully appreciated as the same become better understood from the following detailed description when considered in connection with the annexed drawings in which like reference characters designate like or corresponding parts throughout the several views, and wherein:

FIG. 1 is a schematic view of a liquid chromatograph/mass spectrometer interface in accordance with the present invention;

FIG. 2 is an enlarged cross-sectional view of the area in which the concentrator wire and the flow control carrier wire intersect taken along line 2—2 of FIG. 1.

FIG. 3 is an enlarged schematic view of one end of a capillary tube and flow control carrier wire formed in accordance of a second embodiment of the present invention.

DETAILED DESCRIPTION

Figure 4:
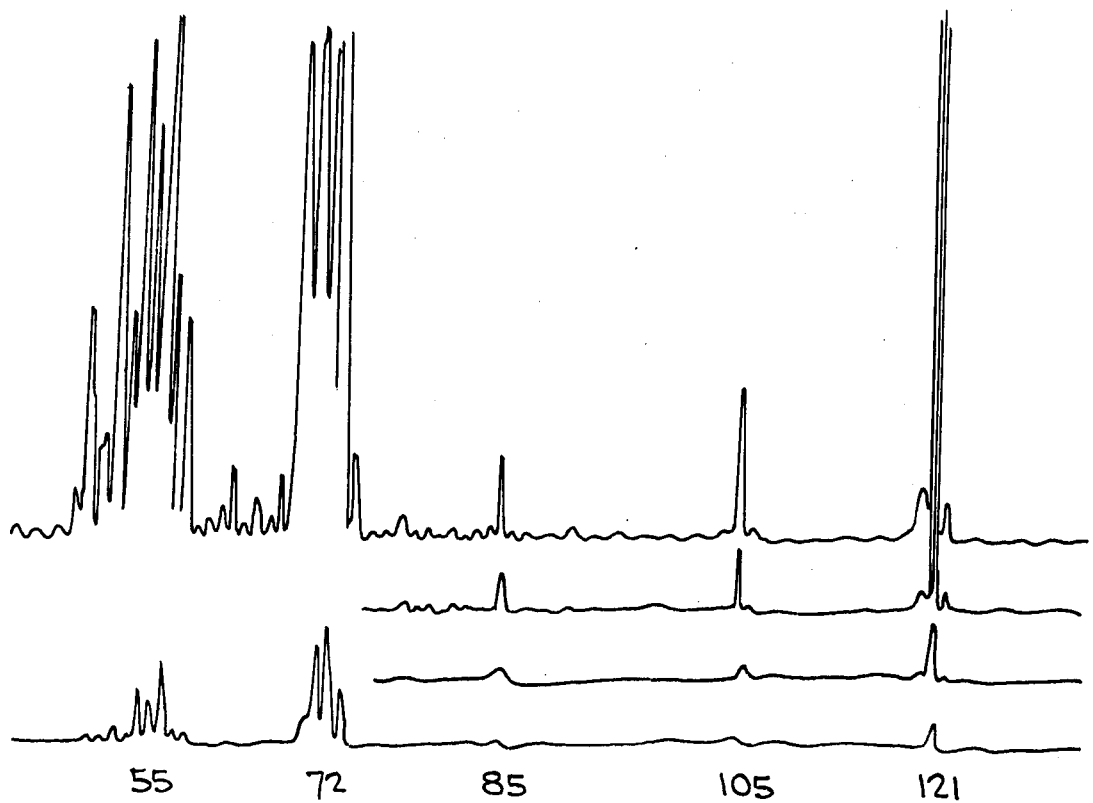
FIG. 4 is a representation of the mass spectrum of acetophenone with n-pentane as the solvent reagent taken by the apparatus of the present invention.

Referring now to FIG. 1 of the drawings, an interface between a liquid chromatograph (not shown) and a mass spectrometer 45 is illustrated. The interface includes a liquid stream transporter 10 comprising an inlet 22 for receiving a liquid stream of effluent from the chromatograph, an inlet 24 for receiving a purge gas, e.g. nitrogen, a glass tube 12 positioned so that the inlets are situated along an upper portion of the tube and a liquid stream-carrying tapered concentrator wire 14 which extends over the entire length of the tube, protruding from the lower end of the tube as well as from a portion of the inlet 22 at the upper end of the tube. The wire preferably comprises several sections, each being of different material and each succeeding section being of a lesser diameter and resistance than the section that is located directly above it. It is important that each section be of a lesser diameter than the section thereabove so that the gradually evaporating stream will be maintained in continuous condition about the wire from one wire end to the other. The embodiment of wire 14 illustrated in FIG. 1 includes an upper section 16 of 0.8 mm stainless steel tubing with a resistance of 5 ohms/m; a central section 18 of 0.6 mm constantan wire with a resistance of 2 ohms/m; and a lower section 20 of 0.3 mm copper wire with a resistance of 0.3 ohms/m.

While a wire is disclosed, this term is not to be taken as limiting the specification as such and other equivalent structures as hollow tubes of small diameter may likewise be used.

The wire must be tapered as illustrated in order that it be continuously wet by the liquid stream thereby being diminished by the heat which is supplied thereto. It is further necessary that the greatest input of heat be supplied to the thickest portion of the wire (which has the greatest liquid flow) and that a lesser amount of heat be supplied to each succeeding wire section of lesser thickness, so that the smallest diameter wire portion (which has the smallest liquid flow thereupon) will receive the least heat input. The heat can be supplied either by an external heating element or heater, which radiates heat directly to the wire and the liquid, or by passing an electric current through the wire 14 which then heats the liquid. When an external heater is used, the sections of wire 14 need not be made of different materials, as the resistance of each section need not be decreased to decrease heat output, as when current is passed through the wire. By so heating the stream, the solvent portion of the liquid stream is partly evaporated, it has been found that a solvent flow of 1 ml/min. from the chromatograph can be concentrated to about 5% of the original input and that a solvent flow of 2 ml/min. can be concentrated to approximately 2-5% of the original input.

Since the vapor from the stream will remain within a container represented by glass tube or envelope 12, it is necessary to provide a purge gas, such as nitrogen, in order to sweep the vapors from the container. Additionally, the specific heat input to the wire can be controlled by a feedback device which reacts to the flow rate of the stream adjacent the bottom of wire 14. Such a feedback device can include a photocell 48.

The interface further includes structure for introducing the now concentrated solution into the mass spectrometer 45. A first solution droplet 31 is illustrated in FIG. 2 adjacent the intersection 30 of concentrator wire 14 and flow control carrier wire 38 and a second droplet 32 is shown adhered to the wires at their intersection, ready to be drawn into the spectrometer. These droplets represent a portion of the original liquid stream of effluent from the chromatograph which remains after the heat has been applied to the continuous stream over the wire. The intersection is situated in a gap 36 located in a stainless steel capillary tube 34. Tube 34 has an inner diameter larger than the diameter of wire 38, e.g. a 1.0 mm tube outer diameter and a 0.12 mm tube inner diameter and a 0.1 mm wire diameter so that there is room for liquid to flow between the wire and the tube towards the spectrometer.

The liquid is drawn through the tube 34 by the high vacuum of the mass spectrometer. Flow can be controlled by a control element 50 which can move the wire 38 longitudinally within the tube, in order to partially occlude the end of the tube and its bore which is adjacent to the spectrometer. By moving thumbscrew 51 of control 50 in either direction, wire 38 is pulled inwardly or outwardly of the base of tube 34, which is attached at one end to one leg of the control. By varying the size of the bore and the flow rate, it is then possible to obtain chemical ionization and/or electron impact spectra with the spectrometer. The spectrometer includes a vacuum flange 47 and an ion source 46.

A glass sleeve insulator 44 can be used to guide the tube 34 into the source of the mass spectrometer. In order to limit the flow rate, the end of the tube 40 can either be plated with nickel or flattened, as illustrated in FIG. 2, to constrict the tube opening. Such a constriction is necessary in order to prevent the solution being moved towards the spectrometer from boiling within the tube before it reaches the end thereof. Furthermore, a copper heat sink 42 can be placed around the tube adjacent to the glass insulator.

The vacuum system of the mass spectrometer 45 is capable of handling large liquid flows, e.g. 5-10 $\mu l$/min. Utilizing this apparatus, chemical ionization spectra have been obtained on 0.1% solutions of acetophenone and benzophenone in pentane, and FIG. 4 illustrates the spectrum of acetophenone achieved.

An alternate means for constructing the tube and wire probe is illustrated in FIG. 3 and provides a tube which is not as easily plugged as the permanently constricted tube of FIGS. 1 and 2. In this embodiment the tube 34 has a cut-away end portion 54 and a wire 38 is formed of tungsten which has a football-shaped piece of silver solder 52 on its end. This end structure must be formed so that solder can be seated in the orifice at the end of the tube in order to vary the flow rate of the liquid therein and to prevent the influx of air when the probe is not in use, e.g., with a 0.075 mm wire, a tube with a 1.0 mm outer diameter, a 0.10 mm inner diameter and a solder ball about 0.5 mm long and having a 0.3 mm diameter is used. Using such measurements to design the apparatus, the flow rate can be varied from approximately 10 $\mu l$/min. to less than 1 $\mu l$/min., and is set so that the pressure above the turbomolecular ion source pump is about $1 \times 10^{-4}$ power Torr.

From the foregoing description, one skilled in the art can easily ascertain the essential characteristics of this invention and without departing from the spirit and scope thereof, can make various changes and modifications of the invention to adapt it to various useages and conditions.

What is claimed is:

1. An interface between a liquid chromatograph and a mass spectrometer for introducing a liquid stream from the chromatograph into the spectrometer, wherein said interface comprises:
   (a) a tapered wire having a first end and a second end, the tapered wire adapted to carry said stream from said chromatograph;
   (b) means for providing heat to the stream in order to cause part of the liquid stream to turn into vapor;
   (c) means for drawing said stream from adjacent said second wire end towards said spectrometer; and
   (d) means for conducting said stream from adjacent said second wire end into said mass spectrometer.

2. An interface between a liquid chromatograph and a mass spectrometer in accordance with claim 1 wherein said tapered wire decreases from a relatively wide diameter at said first end to a relatively narrow diameter at said second end.

3. An interface between a liquid chromatograph and a mass spectrometer in accordance with claim 2 wherein said heating means provides more heat at a relatively wide part of the wire than at a relatively narrow part of the wire.

4. An interface between a liquid chromatograph and a mass spectrometer in accordance with claim 1 wherein said means for providing heat to said stream comprises means for passing electric current through said wire.

5. An interface between a liquid chromatograph and a mass spectrometer in accordance with claim 1 wherein said tapered wire comprises a plurality of materials each having a different diameter.

6. An interface between a liquid chromatograph and a mass spectrometer in accordance with claim 5 wherein said materials comprise stainless steel, constantan and copper.

7. An interface between a liquid chromatograph and a mass spectrometer in accordance with claim 1 wherein said tapered wire is surrounded by a glass container and a flow of gas is provided for purging said vapor from said container.

8. An interface between a liquid chromatograph and a mass spectrometer in accordance with claim 1 wherein said conducting means comprises a capillary tube.

9. An interface between a liquid chromatograph and a mass spectrometer in accordance with claim 8 wherein said capillary tube has a gap at the point at which it crosses said tapered wire.

10. An interface between a liquid chromatograph and a mass spectrometer in accordance with claim 9 wherein said capillary tube has a reduced diameter at one end thereof, said end being adjacent to said mass spectrometer.

11. An interface between a liquid chromatograph and a mass spectrometer in accordance with claim 8 wherein a flow control carrier wire is situated within the tube and partially occludes the tube at one end thereof.

12. An interface between a liquid chromatograph and a mass spectrometer in accordance with claim 11 further including means for moving said flow control wire longitudinally within said tube.

13. An interface between a liquid chromatograph and a mass spectrometer in accordance with claim 11 wherein said carrier wire has a ball of solder on one end thereof adjacent to said one tube end, said ball serving to partially constrict said tube end.

14. An interface between a liquid chromatograph and a mass spectrometer in accordance with claim 1 further including means for sensing the flow rate of said stream adjacent said second wire end.

15. A method of conducting a liquid stream from a liquid chromatograph and introducing the stream into a mass spectrometer, said method comprising:
 (a) transporting a liquid stream from one end of a tapered wire to the other end of said wire;
 (b) heating said stream so as to evaporate a portion of said solvent from said liquid stream; and
 (c) drawing and conducting said liquid stream from adjacent said second end of said wire along the inside of a tube towards said mass spectrometer.

16. A method of conducting a liquid stream in accordance with claim 15 wherein said first wire end has a relatively wide diameter and said second wire end has a relatively narrow diameter.

17. A method of conducting a liquid stream in accordance with claim 15 wherein said solvent portion is converted into a vapor which is purged from a container surrounding said wire by a flow of purging gas.

18. A method of conducting a liquid stream in accordance with claim 15 which comprises conducting and drawing said liquid through said tube by a high vacuum created by said mass spectrometer.

19. A method of conducting a liquid stream in accordance with claim 18 further comprising controlling the flow of said liquid being drawn by a longitudinally moving pointed wire within said tube.

20. A method of conducting a liquid stream in accordance with claim 15 wherein said tube has a ball of solder on one end thereof adjacent to one end of said tube.

21. A method of conducting a liquid stream in accordance with claim 15 wherein said liquid stream is drawn from said tapered wire where said wire intersects a gap in said tube.

22. A method for conducting a liquid stream in accordance with claim 15 which comprises heating said wire proportionally to its diameter whereby more heat is provided to a relatively wide portion of the wire and less heat is provided to a relatively narrow portion thereof.

23. A method for conducting a liquid stream in accordance with claim 15 comprising heating said wire by passing electric current therethrough.

24. A method for conducting a liquid stream in accordance with claim 15 further comprising maintaining said liquid stream in a continuous condition about said wire.

25. A continuous-flow solution concentrator for removing solvent from a liquid stream which comprises:
 (a) a tapered wire for transporting said liquid stream, said wire decreasing from a first end having a relatively wide diameter to a second end having a relatively narrower diameter;
 (b) means for providing heat to the stream such that more heat is provided to a portion of the stream at a relatively wide part of the wire than to a portion of the stream at a relatively narrow part of the wire, said heating means vaporizing a portion of the liquid stream; and
 (c) a container surrounding said wire.

26. A continuous-flow solution concentrator in accordance with claim 25 further comprising means for purging the vapor from said container.

27. A continuous-flow solution concentrator in accordance with claim 25 wherein said tapered wire is comprised of a plurality of different materials each having a different diameter.

28. A continuous-flow solution concentrator in accordance with claim 25 wherein said materials comprise stainless steel, constantan and copper.

29. A continuous-flow solution concentrator in accordance with claim 25 wherein said container is a glass envelope and said sweeping means comprises a flow of gas.

30. A continuous-flow solution concentrator in accordance with 25 wherein said heating means comprises means for passing an electric current through said wire.

31. A method for removing solvent from a continuously flowing liquid stream which comprises:
(a) conducting said liquid stream along a tapered wire which decreases in diameter from a relatively wide diameter at one end to a relatively narrow diameter at its second end;
(b) providing heat to said stream in order to heat said stream and convert a portion of said stream into vapor, whereby more heat is provided to a portion of the stream at a relatively wide portion of the wire than to a portion of the stream at a relatively narrow portion thereof; and
(c) sweeping the vapors from a container positioned around said wire.

32. A method for removing solvent from a liquid stream in accordance with claim 31 comprising sweeping said vapors from said container by flowing purge gas therethrough.

33. A method for removing solvent from a liquid stream in accordance with claim 31 wherein said purge gas is nitrogen.

34. A method for removing solvent from a liquid stream in accordance with claim 31 comprising heating said wire by passing an electric current therethrough.

35. A method for removing solvent from a liquid stream in accordance with claim 31 further comprising maintaining said liquid stream in a continuous condition about said wire.

* * * * *